(12) United States Patent
Hirai et al.

(10) Patent No.: US 8,371,859 B2
(45) Date of Patent: Feb. 12, 2013

(54) INSTRUMENT FOR SUPPRESSING DRUG CRAVING AND KIT FOR SUPPRESSING DRUG CRAVING

(75) Inventors: Shinji Hirai, Chiba (JP); Mitsuru Hasegawa, Osaka (JP); Takeshi Ohguro, Osaka (JP)

(73) Assignees: National Hospital Organization, Tokyo (JP); Nipro Corporation, Osaka-shi, Osaka (JP)

( * ) Notice: Subject to any disclaimer, the term of this patent is extended or adjusted under 35 U.S.C. 154(b) by 245 days.

(21) Appl. No.: 12/734,104

(22) PCT Filed: Oct. 15, 2008

(86) PCT No.: PCT/JP2008/068662
§ 371 (c)(1),
(2), (4) Date: Apr. 9, 2010

(87) PCT Pub. No.: WO2009/051136
PCT Pub. Date: Apr. 23, 2009

(65) Prior Publication Data
US 2010/0211018 A1    Aug. 19, 2010

(30) Foreign Application Priority Data

Oct. 15, 2007   (JP) .................................. 2007-268142

(51) Int. Cl.
*G09B 23/28* (2006.01)
(52) U.S. Cl. ........ 434/272; 434/267; 604/403; 604/411; 604/415; 604/416
(58) Field of Classification Search .................. 604/506, 604/82, 403, 411, 415, 416; 434/268, 272, 434/267
See application file for complete search history.

(56) References Cited

U.S. PATENT DOCUMENTS
2006/0269906 A1* 11/2006 White .......................... 434/262

FOREIGN PATENT DOCUMENTS
JP          57-59197 Y2    12/1982
JP           61-4393 Y2     2/1986

OTHER PUBLICATIONS

Japanese Patent Office Search Report dated Jan. 20, 2009 (1 page).
Form PCT/ISA/210 dated Jan. 20, 2009 (2 pages).
Form PCT/ISA/220 dated Jan. 20, 2009 (4 pages).
Form PCT/ISA/237 dated Jan. 20, 2009 (3 pages).
Monthly "Psychiatry" vol. 8, No. 6, issued on Jun. 28, 2006, "Treating Idiosyncrasy of Stimulant Drug Addiction" by Shinju Hirai, pp. 455-463.

*Primary Examiner* — Laura Bouchelle
(74) *Attorney, Agent, or Firm* — Flynn, Theil, Boutell & Tanis, P.C.

(57) ABSTRACT

The kit for suppressing drug craving K is used by connecting an instrument for suppressing drug craving 1 to a syringe 2 and the instrument for suppressing drug craving 1 has a cylindrical housing 11, a pouch 12 provided in the housing and containing pseudo-blood B and a connecting member 13 with which the distal end of a syringe is coupled and which cause the syringe to communicate with the interior of the pouch. When the syringe accommodating pseudo-drug M is connected to the instrument and the plunger is moved forward (pseudo-priming), the pseudo-drug M flows into a pouch and the pouch inflates (FIG. 2(*b*)), and if the plunger 4 is pulled back from this condition, the pouch 12 deflates and the pseudo-blood B flows back from the pouch 12 to the syringe 2 (flashback) (FIG. 2(C)).

6 Claims, 2 Drawing Sheets

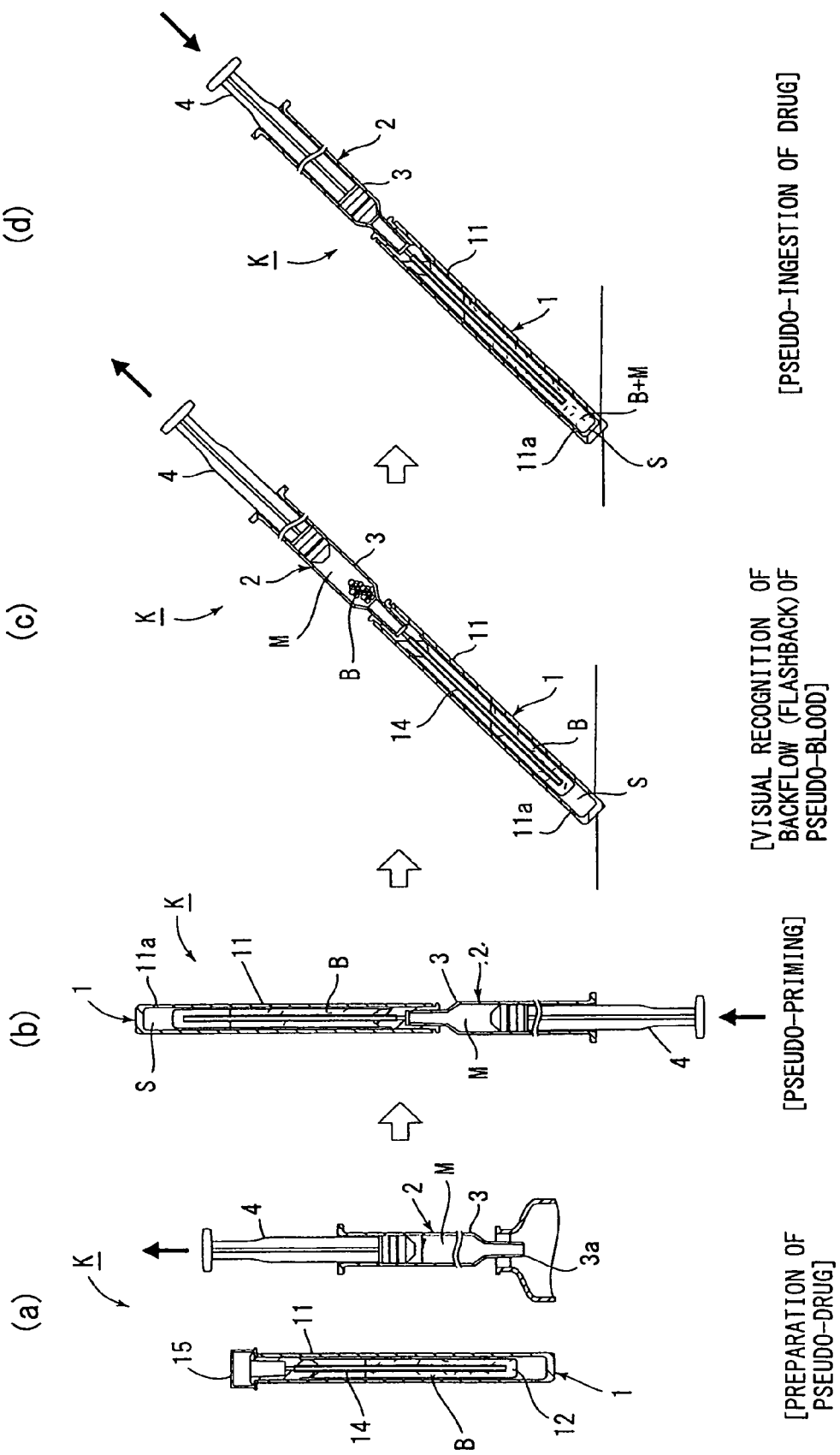

INSTRUMENT FOR SUPPRESSING DRUG CRAVING AND KIT FOR SUPPRESSING DRUG CRAVING

TECHNICAL FIELD

The present invention relates to an instrument for suppressing drug craving and a kit for suppressing drug craving, and more specifically, to an instrument for suppressing drug craving and a kit for suppressing drug craving used for therapy of drug addicts.

BACKGROUND ART

Conventionally, therapy of drug addicts of repeated abuse of drugs including stimulant drugs is conducted, but there are no established therapeutic methods yet and various therapeutic methods are being tried.

Among such therapeutic methods, there is a proposal of a method of repeating a process of giving conditional stimuli suggestive of use of a drug to a drug addict and actually preventing the drug addict from administering the drug to cause the drug addict to lose any significance of the conditional stimuli and eventually suppress conditioned reflex (Non-Patent Document 1).

According to this Non-Patent Document 1, in the process from acquiring the drug to actually administering the drug, looking at the drug dealer's face, the pack containing the drug or syringe or the like, the drug addict is exposed to conditional stimuli and these conditional stimuli form a conditioned reflex circuit in the brain.

Therefore, although the drug addict does not administer the drug, the drug addict is believed to crave for the drug by means of conditioned reflex when he/she looks at the drug itself, the drug dealer's face, the pack containing the drug or syringe or the like.

Repeating the process of giving such conditional stimuli to the drug addict and actually not allowing him/her to administer the drug is expected to make less the significance of the conditional stimuli and thereby suppress the craving for the drug by means of conditioned reflex.

Here, in the above described conditional stimuli, examples of those having a great influence on the drug addict include the act itself of the drug addict operating the syringe and administering the drug, causing the blood to flow back into the syringe (flashback) to confirm whether or not the needle is inserted into the blood vessel and visually recognizing the insertion.

To treat by giving such conditional stimuli to the drug addict, a saline instead of the drug may be put into the syringe to let the drug addict administer this saline or visually recognize the backflow of the blood into the syringe. Non-Patent Document 1: Monthly "Psychiatry" Vol. 8, No. 6, issued on Jun. 28, 2006, "Treating Idiosyncrasy of Stimulant Drug Addiction" by Shinji Hirai

DISCLOSURE OF THE INVENTION

Problems to be Solved by the Invention

However, only health care professionals such as medical doctors are authorized to conduct the act of inserting the needle into drug addicts and providing this therapy for many drug addicts would require enormous amounts of efforts and time for the health care professionals.

Furthermore, since the needle is used for the therapy, an inadvertent accident may occur due to careless use of the needle.

In view of the above described problems, the present invention provides an instrument for suppressing drug craving and a kit for suppressing drug craving that can be safely used even by people other than health care professionals or drug addicts themselves.

Means for Solving the Problems

That is, the instrument for suppressing drug craving according to the invention includes a cylindrical housing, a pouch provided inside the housing and containing pseudo-blood therein and a connecting member provided in the housing, to which a distal end of a syringe is connected and which allows the syringe to communicate with an interior of the pouch, wherein the pouch is inflated in the housing when a liquid is supplied from the syringe via the connecting member and contracted when the pseudo-blood in the pouch is sucked into the syringe.

Furthermore, the kit for suppressing drug craving according to the invention includes the instrument for suppressing drug craving described above and a syringe.

Advantages of the Invention

According to the instrument for suppressing drug craving and the kit for suppressing drug craving according to the above described invention, when a liquid is supplied from the syringe, the pouch is inflated and the liquid in the syringe is accommodated, and the drug addict can thereby have a simulated experience of administration of the drug by operating the syringe.

Furthermore, when pulled back by the syringe, the pouch is contracted and pseudo-blood is flown back into the syringe, and the drug addict can thereby visually recognize that the pseudo-blood flows back into the syringe (flashback).

Thus, according to the instrument for suppressing drug craving of the present invention, it is possible to give conditional stimuli to the drug addict without using any needle and thereby safely conduct a therapy of the drug addict without depending on health care professionals.

BRIEF DESCRIPTION OF THE DRAWINGS

FIG. 2 is a diagram illustrating a therapeutic method using the kit for suppressing drug craving.

DESCRIPTION OF SYMBOLS

Figure 1:
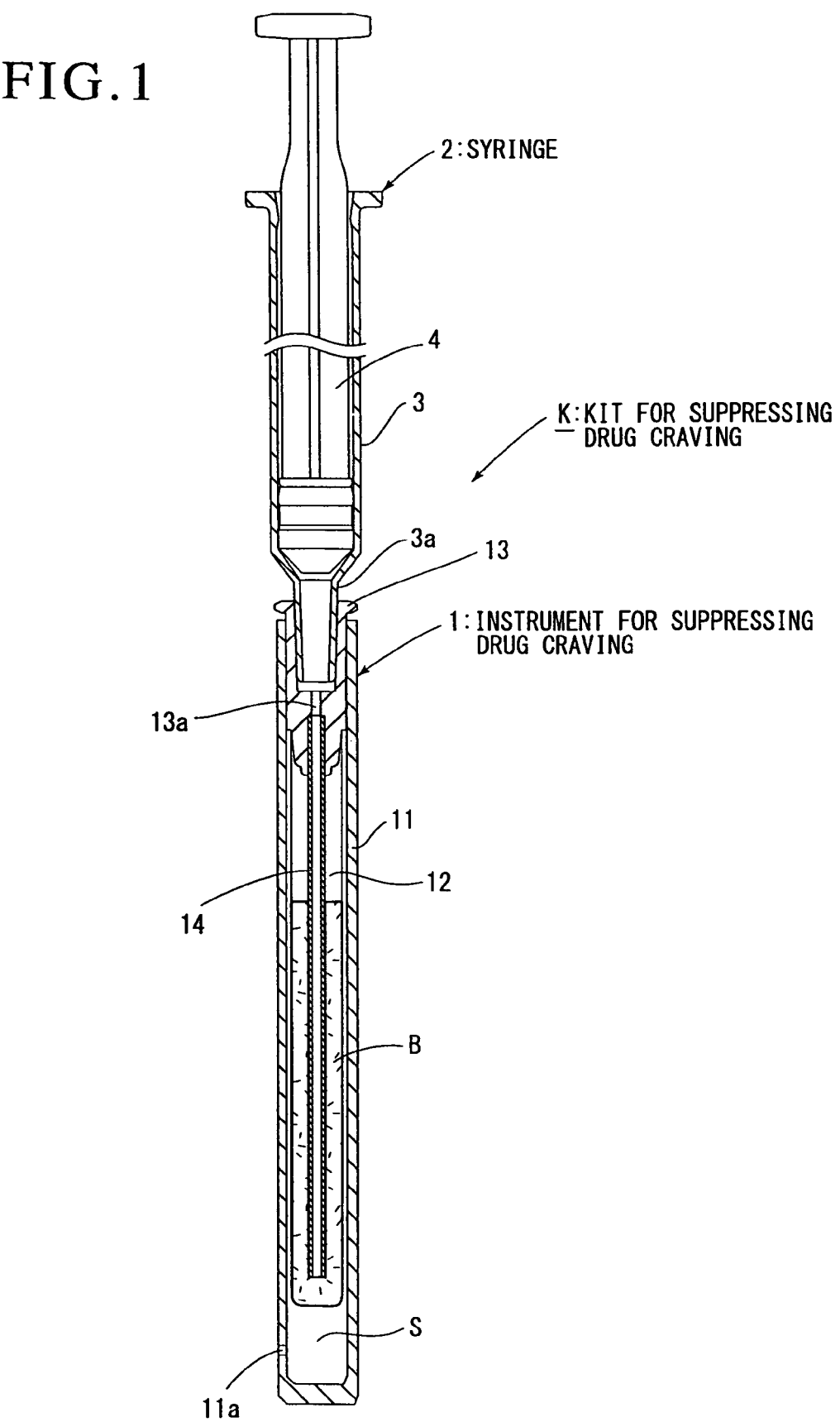
FIG. 1 is a cross-sectional view of a kit for suppressing drug craving according to the present embodiment.

1 Instrument for suppressing drug craving
2 Syringe
3 Body
4 Plunger
11 Housing
11a Through hole
12 Pouch
13 Connecting member
14 Tube
B Pseudo-blood
K Kit for suppressing drug craving
M Pseudo-drug
S Space

BEST MODE FOR CARRYING OUT THE INVENTION

Hereinafter, an embodiment illustrated in the drawings will be described. FIG. 1 illustrates a kit for suppressing drug craving K comprising an instrument for suppressing drug craving 1 used for therapy of a drug addict and a syringe 2 connected to the instrument for suppressing drug craving 1.

First, the syringe 2 comprises a body 3 that accommodates pseudo-drug M, which will be described later, and a plunger 4 provided in the body 3 in a manner movable forward or backward. Although a connecting part 3a having reduced diameter is formed at an end of the body 3, the syringe is configured without any needle.

Furthermore, the body 3 is made of a transparent member and allows the drug addict to visually recognize the pseudo-drug M and pseudo-blood B therein.

Next, the instrument for suppressing drug craving 1 is provided with a cylindrical housing 11, a pouch 12 provided in the housing 11 and accommodating the pseudo-blood B therein and a connecting member 13 provided in the housing 11, with which the connecting part 3a of the syringe 2 is coupled.

The housing 11 is a closed-end cylindrical member and made of an opaque material or coated with opaque paint. Thus, the pouch 12 and the pseudo-blood B therein cannot be visually recognized from the outside of the housing 11.

The instrument for suppressing drug craving 1 is fitted to the syringe 2 instead of a needle, and the shape of the housing 11 is preferably as slim as possible and the distal end thereof is made flat in consideration of safety of health care professionals and drug addicts.

Furthermore, a desired space S is formed between the interior of the housing 11 and the pouch 12 so as to allow the pouch 12 to inflate when the pseudo-drug M or the like flows into the pouch 12 as will be described later.

Furthermore, a through hole 11a is provided at a position where the space S is formed so as to allow the outside of the housing 11 and the space S to communicate with each other and discharge the air in the space S when the pouch 12 is inflated so as not to block the inflation of the pouch 12.

The pouch 12 is open toward the opening side at the proximal end of the housing 11 and contains red ink as the pseudo-blood B.

Furthermore, the pouch 12 is made of a material not having elasticity such as polyethylene, polypropylene and is designed not to contract itself so as not to discharge the stored pseudo-blood B to the outside.

Furthermore, when the instrument for suppressing drug craving 1 is not used, the pouch 12 stays slightly contracted. In other words, the pouch 12 is not completely filled with the pseudo-blood B and the pouch 12 is designed to inflate when the pseudo-drug M in the syringe 2 is supplied to the pouch 12.

The connecting member 13 is fixed to the opening of the housing 11 and the connecting part 3a of the syringe 2 is connected at the proximal end of the connecting member 13. Furthermore, the opening of the pouch 12 is fluid-tightly adhered and fixed to a part projecting toward the inside of the housing 11 of the connecting member 13.

Furthermore, a communication hole 13a is provided in the center of the connecting member 13 and a cylindrical tube 14 communicating with the communication hole 13a is provided at a distal end of the connecting member 13. The communication hole 13a and the tube 14 allow the syringe 2 and the pouch 12 to communicate with each other.

The distal end of the tube 14 is provided in the vicinity of the distal end of the pouch 12 and if the instrument is used with the proximal end of the housing 11 up, the gas inside the pouch 14 rises upward, and therefore even if the liquid inside the pouch 12 is sucked using the syringe 2 in that condition, the gas never flows into the syringe 2 via the tube 14.

Furthermore, when the syringe 2 is not connected, a desired cap 15 (see FIG. 2) can be attached to the connecting member 13, making it possible to prevent the pseudo-blood B of the pouch 12 from flowing out.

Hereinafter, the therapeutic method for the drug addict using the kit for suppressing drug craving K will be described using FIG. 2. This therapeutic method can be performed for drug addicts by health care professionals or people other than health care professionals or the drug addicts themselves can perform the method. Hereinafter, a case will be described where a drug addict himself/herself uses the kit.

FIG. 2(a) illustrates a situation in which the pseudo-drug M is prepared in the syringe 2 and the instrument for suppressing drug craving 1 is made ready for use.

First, the instrument for suppressing drug craving 1 is not connected to the syringe 2, the plunger 4 is detached from the body 3 and nothing is accommodated in the body 3.

From this condition, the drug addict charges a proper amount of powdered salt that imitates a drug or the like from the proximal end of the body 3 of the syringe 2 first and then fits the plunger 4 into the syringe from the proximal end of the body 3 (this operation is not shown).

Next, while keeping the charged powdered pseudo-drug from dropping from the connecting part 3a, the drug addict inserts the connecting part 3a of the body 3 into a desired container storing a solution, for example, saline, pulls back the plunger 4 and introduces the desired saline into the body 3.

The drug addict then orients the distal end of the syringe 2 upward, keeps the saline inside from spilling out, further rotates the syringe 2 to thereby get the powdered pseudo-drug mixed with the saline and obtains a liquid pseudo-drug M.

On the other hand, the cap 15 is attached to the connecting member 13 of the instrument for suppressing drug craving 1 to prevent the pseudo-blood B from flowing out of the pouch 12.

From this condition, with the distal end of the housing 11 facing downward, that is, the cap 15 facing upward, the drug addict taps the instrument for suppressing drug craving 1 several times to cause the pseudo-blood B inside the pouch 12 to move downward.

In this series of operations, looking at the powdered pseudo-drug or syringe 2 and preparing the pseudo-drug M in the syringe 2 or the like constitute conditional stimuli for the drug addict, which invokes a craving for the drug.

FIG. 2(b) illustrates a situation in which the syringe 2 is connected to the instrument for suppressing drug craving 1 and pseudo-priming is performed.

To be more specific, the cap 15 is removed from the instrument for suppressing drug craving 1 and the connecting part 3a of the syringe 2 is connected to the connecting member 13.

In this case, when the saline is sucked into the syringe 2 in the operation in FIG. 2(a), a gas may enter the syringe 2, but when the drug is actually administered, "priming" needs to be performed to remove this gas to prevent the gas from flowing into the body.

Here, pseudo-priming is performed in imitation of this priming and the drug addict slightly moves the plunger 4 forward as in the case of the actual operation. As a result, the gas in the syringe 2 and part of the pseudo-drug M flow into the pouch 12 via the connecting member 13 and the tube 14.

In this way, the pouch 12 inflates to some extent through the inflow of the gas and the pseudo-drug M, and on the other hand, the space S of the housing 11 reduces and the amount of gas corresponding thereto is discharged through the through hole 11a formed in the housing 11.

Thus, the space S never becomes a positive pressure by discharging the gas from the space S, which prevents blockage of the inflation of the pouch 12 and does not block the forward movement of the plunger 4.

Moreover, performing pseudo-priming in this operation constitutes a conditional stimulus for the drug addict and invokes a craving for the drug.

FIG. 2(c) illustrates a situation in which the drug addict is allowed to visually recognize pseudo-flashback.

To be more specific, the drug addict holds the instrument for suppressing drug craving 1 connected to syringe 2 with the distal end of the housing 11 downward and presses the skin close to the vein by the distal end of the housing 11. This allows the drug addict to experience the act of inserting the needle into the blood vessel.

Next, the drug addict pulls back the plunger 4 of the syringe 2 while keeping the distal end of the housing 11 in contact with the skin. The interior of the syringe 2 then becomes a negative pressure, the pseudo-blood B in the pouch 12 is introduced via the connecting member 13 and the tube 14, and the pouch 4 is contracted.

The introduced pseudo-blood B flows into the syringe 2, and because the pseudo-blood B is colored in red, the drug addict can visually recognize the backflow (flashback) of the pseudo-blood B inside the syringe 2.

Visual recognition of the flashback of blood is performed to check whether or not the needle of the syringe is inserted in the vein when the drug addict actually administers the drug and is considered to be especially great as the conditional stimuli given to the drug addict.

Visual recognition of the flashback of blood is a great conditional stimulus for the drug addict and invokes a larger craving for the drug.

In the operation of this FIG. 2(c), the tube 14 is provided up to the vicinity of the distal end of the pouch 12 and since the instrument for suppressing drug craving 1 is used face down, the gas flown into the pouch 12 during pseudo-priming in FIG. 2(b) moves up to the top of the pouch 12.

Thus, when the plunger 4 is pulled back, only the pseudo-drug M stored at the bottom of the pouch 12 is sucked and the gas never flows back into the syringe 2, and the drug addict can thereby have a simulated experience of flashback.

Furthermore, some drug addicts may visually recognize this flashback many times and may move the plunger 4 to and fro a plurality of times.

Even in such a case, if the plunger 4 is moved forward, the pseudo-drug flows into the pouch 12 and if the plunger is pulled back, the pseudo-blood flows back into the syringe, and the drug addict is thereby allowed to visually recognize flashback any number of times.

FIG. 2(d) illustrates a situation in which the drug addict pushes in the plunger 4 to the end and administers the drug in a pseudo-manner.

When the plunger 4 is pushed in to the end, the pseudo-drug M and the pseudo-blood B in the syringe 2 flow into the pouch 12 via the connecting member 13 and the tube 14 and the pouch 12 inflates.

The pouch 12 has a volume enough to accommodate the pseudo-blood B and the pseudo-drug M and is contracted beforehand, and can thereby accommodate all the pseudo-drug M supplied.

On the other hand, when the pouch 12 inflates, the volume of the space S formed in the housing 11 decreases, but the gas in the space S is discharged from the through hole 11a and the pushing of the plunger 4 is never blocked.

Moreover, the operation of pushing the plunger 4 constitutes a conditional stimulus for the drug addict and causes the automatic nerve to go out of order, but since the drug is actually not administered and the drug addict is prevented from being filled with uplifting feeling or the like by the drug itself.

After that, even when the conditional stimulus produced by the above described operation is given through repetition of such a therapeutic method, since uplifting feeling or the like with the actual drug is not obtained, the significance of these conditional stimuli diminishes.

Suppressing a craving for the drug by means of conditioned reflex then leads to therapy of the drug addict.

Furthermore, since the above described therapeutic method does not use any needle, even people other than health care professionals who are not originally authorized to insert the needle can perform the above described therapy.

Furthermore, since no needle is provided, the drug addict himself/herself can use the kit and since the drug addict himself/herself performs the above described operation, it is possible to achieve a therapeutic effect more effectively than health care professionals do.

In the above described embodiment, the distal end of the housing 11 of the instrument for suppressing drug craving 1 is substantially flat, but by providing the distal end with a convex part and causing the distal end of the housing 11 in FIGS. 2(c) and (d) above to be pressed against the skin of the drug addict, it is possible to give a sense similar to sting pain and thereby give a conditional stimulus.

The invention claimed is:
1. An instrument for suppressing drug craving comprising:
 a syringe;
 a housing formed into an elongated cylindrical shape having a thickness equal to or less than that of the syringe;
 a pouch provided inside the housing and containing a pseudo-blood; and
 a connecting member provided at an opening of the housing, with which a distal end of the syringe is coupled and which allows the syringe to communicate with an interior of the pouch,
 wherein the pouch is inflated in the housing when a liquid is supplied from the syringe via the connecting member, contracted when the pseudo-blood in the pouch is sucked into the syringe and formed into a elongated cylindrical shape with a bottom in a longitudinal direction of the housing, an opening of the pouch being connected to the connecting member, a linear tube being provided inside the pouch, an end of the tube being connected to the connecting member and the syringe communicating with the interior of the pouch via the connecting member and the tube.

2. The instrument for suppressing drug craving according to claim 1, wherein the interior of the pouch causes air to remain inside rather than being filled completely by pseudo-blood, the pouch is arranged to inflate when liquid is supplied to it by the syringe, a distal end of the tube extends to a position neighboring a distal end of the pouch and
 air flows to an upper part of the pouch when using the instrument by turning a rear end of the housing upward to prevent the liquid in the pouch from flowing into the syringe via the tube, even if under a vacuum by the syringe.

3. The instrument for suppressing drug craving according to claim 2, wherein the pouch is made of a material having no elasticity.

4. The instrument for suppressing drug craving according to claim 3, wherein the housing is formed in a cylindrical shape having the bottom, a through hole being formed at the distal end of the housing so as to be able to discharge the air within the pouch via the through hole when the pouch is inflated.

5. The instrument for suppressing drug craving according to claim 4, wherein the housing is opaque so that the interior of the housing cannot be seen from outside, and flowing out of the pseudo-blood within the pouch is prevented by mounting a cap to the connecting member when the syringe is not connected.

6. The instrument for suppressing drug craving according to claim 5, wherein a convex part is provided at a distal end of the housing and the convex part is pressed against a user.

* * * * *